(12) United States Patent
Ettema et al.

(10) Patent No.: US 8,529,949 B2
(45) Date of Patent: Sep. 10, 2013

(54) PHARMACEUTICAL TABLETS OF CRYSTALLINE TYPE II ARIPIPRAZOLE

(75) Inventors: Gerrit J. B. Ettema, Nijmegen (NL); Raymond J. H. Westheim, Oss (NL); Faysal Kalmoua, Oss (NL); Korinde Annemarie Jansen, Loo (NL); Farid Abedin Dorkoosh, Utrecht (NL)

(73) Assignee: Synthon BV, Nijmegen (NL)

( * ) Notice: Subject to any disclaimer, the term of this patent is extended or adjusted under 35 U.S.C. 154(b) by 2154 days.

(21) Appl. No.: 11/377,400

(22) Filed: Mar. 17, 2006

(65) Prior Publication Data

US 2006/0257471 A1    Nov. 16, 2006

Related U.S. Application Data

(60) Provisional application No. 60/662,552, filed on Mar. 17, 2005, provisional application No. 60/692,557, filed on Jun. 22, 2005, provisional application No. 60/739,640, filed on Nov. 26, 2005.

(51) Int. Cl.
*A61K 9/20* (2006.01)

(52) U.S. Cl.
USPC .......................................... 424/465; 424/464

(58) Field of Classification Search
None
See application file for complete search history.

(56) References Cited

U.S. PATENT DOCUMENTS

| 4,734,416 A | 3/1988 | Banno et al. |
|---|---|---|
| 5,006,528 A | 4/1991 | Oshiro et al. |
| 2002/0076437 A1 * | 6/2002 | Kothari et al. ............... 424/465 |
| 2004/0058935 A1 | 3/2004 | Bando et al. |
| 2005/0203299 A1 * | 9/2005 | Aronhime et al. ............ 544/262 |
| 2005/0245539 A1 * | 11/2005 | Mendla et al. .......... 514/254.06 |
| 2006/0142299 A1 | 6/2006 | Ettema et al. |
| 2006/0142579 A1 | 6/2006 | Ettema et al. |

FOREIGN PATENT DOCUMENTS

| EP | 367141 | 1/1996 |
|---|---|---|
| WO | WO 03/26659 | 4/2003 |
| WO | WO 03/026659 A1 * | 4/2003 |
| WO | WO 2005/058835 A2 | 6/2005 |

OTHER PUBLICATIONS

"Study on Crystal Transformation of Aripiprazole" The Fourth Japan-Korea Symposium on Separation Technology (1996), pp. 937-940.

* cited by examiner

*Primary Examiner* — Susan Tran
(74) *Attorney, Agent, or Firm* — Mark R. Buscher

(57) ABSTRACT

Crystalline aripiprazole Type II can be formulated into pharmaceutical tablets having reduced dissolution profile variability upon storage.

17 Claims, 3 Drawing Sheets

XRPD spectrum (Type II)

PHARMACEUTICAL TABLETS OF CRYSTALLINE TYPE II ARIPIPRAZOLE

This application claims the benefit of priority under 35 U.S.C. §119(e) from each of (1) U.S. provisional application 60/662,552, filed Mar. 17, 2005, (2) U.S. provisional application 60/692,557, filed Jun. 22, 2005, and (3) U.S. provisional application 60/739,640, filed Nov. 26, 2005, each of which is incorporated herein by reference.

BACKGROUND OF THE INVENTION

The present invention relates to pharmaceutical tablet compositions that contain crystalline aripiprazole Type II and pharmaceutically acceptable excipients.

Aripiprazole or more properly 7-[4-[4-(2,3-dichlorophenyl)-1-piperazinyl]butoxy]-3,4-dihydrocarbostyril, is a compound of the formula (1).

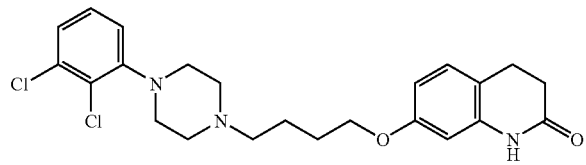

(1)

It is a commercially marketed, pharmaceutically active substance useful for treatment of schizophrenia and bipolar disorder. It is disclosed in EP 367141/U.S. Pat. No. 5,006,528. The commercially marketed product is the free base of the title compound (1).

Solid state aripiprazole was prepared in U.S. Pat. No. 5,006,528 by a two-fold recrystallization of crude aripiprazole from ethanol resulting in colorless flake crystals having a melting point of 139-139.5° C. In an article of Aoki (Study on Crystal Transformation of Aripiprazole, The Fourth Japan-Korea Symposium on Separation Technology, p.937 ff (1996)), this solid state form was designated as Type I aripiprazole and identified as an anhydrate. Aoki also teaches that the Type I aripiprazole may be converted into a Type II aripiprazole by heating at 130-140° C. for 15 hours. This product is also an anhydrate with a melting point of 150° C. When both Type I and Type II aripiprazole were recrystallized from an alcoholic solvent containing water up to 20%, the product was an aripiprazole hydrate labeled as Type III by Aoki. Type III aripiprazole can be converted into Type I by heating at 80° C.

WO 03/26659 (EP 1330249) teaches that Type I aripiprazole, the alleged original solid form of aripiprazole, is significantly hygroscopic. In an effort to find a form of aripiprazole having reduced hygroscopicity and better processing qualities, seven crystalline forms (A-G) were described.

Hydrate Form A is taught as a useful intermediate for making anhydrate forms. Hydrate Form A can be prepared by milling Aoki's hydrated Type III. Contrary to the conventional Form III hydrate, the Hydrate Form A does not exhibit sharp dehydration endothermic peak at 123.5° C. at TGA, but has a gradual endothermic peak between 60-120° C.

Anhydrous Form B, which seems to be the preferred crystalline form, is not hygroscopic; i.e., less than 0.4% water uptake in 24 hours, and is a stable crystalline form. It can be prepared by heating the Hydrated Form A, preferably at 90-125° C. for 3-50 hours or by heating the Type I/Type II aripiprazole at 90-125° C. Although the Anhydrate Form B of WO 03/26659 is not hygroscopic, it suffers from being unsuitable for milling. Specifically, if milling is attempted in order to create small particle sizes such as 50 microns or less, the milled substance tends to adhere to the milling machine making an industrial process difficult. To overcome this problem, WO 03/26659 teaches forming Hydrate Form A aripiprazole, milling the Hydrate Form A to the desired size and then heat converting to Anhydrate Form B.

The other anhydrate forms disclosed therein are briefly summarized below:

Form C: Prepared by heating an aripiprazole anhydrate to 140-150° C. Endothermic peak around 150.2° C.

Form D: Prepared by recrystallization of aripiprazole anhydrate from toluene. Endothermic peaks at 136.8 and 141.6° C.

Form E: Prepared by double heating, dissolving, and crystallizing aripiprazole in acetonitrile with crystallization at about 70° C. Endothermic peak at 146.5° C.

Form F: Prepared by heating a suspension of aripiprazole anhydrate in acetone. Endothermic peaks at 137.5 and 149.8° C.

Form G: Prepared by putting glassy state of aripiprazole anhydrate in a sealed vessel and keeping it at room temperature for at least 2 weeks. Exothermic peak at 122.7° C., endothermic peak at 141.0° C.

More recently techniques for crystallizing Type II aripiprazole directly from a solution were disclosed in U.S. Provisional application Serial Nos. 60/662,552, filed Mar. 17, 2005, and 60/692,557, filed Jun. 22, 2005; the entire contents of each being incorporated herein by reference. In general the Type II was found to be obtainable by precipitation from 2-propanol, dimethyl sulfoxide, or tetrahydrofuran, with a mixture of 2-propanol and ethyl acetate being a preferred embodiment, especially at somewhat elevated temperatures. Similarly, WO2005/058835 also purports to have directly crystallized Type II aripiprazole.

Although various polymorphs of crystalline aripiprazole are known, it is believed that the commercial aripiprazole product uses Type I aripiprazole. However, the commercial product apparently suffers from moisture sensitivity in that the U.S. product is packaged with a large amount of desiccant (3 mg instead of the usual 2 mg desiccant) and the EU product is packaged in moisture protecting aluminum-aluminum blisters.

It would be desirable to form an aripiprazole tablet composition that is less moisture sensitive than the current commercial product.

SUMMARY OF THE INVENTION

The present invention is based on the discovery that crystalline Type II aripiprazole forms pharmaceutical tablet compositions having improved stability in comparison to the commercially available aripiprazole tablet, which presumably contains Type I. Accordingly a first aspect of the invention relates to a pharmaceutical composition in the form of a tablet, comprising 1 to 50 mg of aripiprazole Type II and pharmaceutically acceptable excipients. The excipients generally include (a) one or more polyol fillers, such as lactose, sorbitol, mannitol, etc.; (b) one or more binders, such as microcrystalline cellulose, hydroxylpropyl cellulose, PVP, starch, etc.; (c) one or more disintegrants, such as sodium starch glycolate, crosspovidone, crosscarmelose sodium, etc.; and (d) a lubricant, such as magnesium stearate. Generally the aripiprazole is unmilled and typically has an average particle size of less than 40 microns. In terms of particle size distribution, the $d_{90}$ is typically not greater than 70 microns and more typically not greater than 50 microns.

DETAILED DESCRIPTION OF THE INVENTION

The invention is based on a surprising finding that tablets containing aripiprazole Type II have improved stability under storage conditions. In particular, it was discovered that commercial tablets of aripiprazole can show a pronounced change in dissolution profile in acetate buffer media of pH 4.5 after being stored in open dish at 40° C. No such change was observed, however, in the dissolution in simulated gastric fluid (SGF) of pH 1.2. The acetate buffer solution generally predicts dissolution in a patient's stomach that has food ("fed" condition) while the SGF is used to predict dissolution in a patient's stomach with no food ("fasting" condition). The change in release profile after exposure to air suggests that the commercial product may not deliver the intended dose of aripiprazole to a fed patient after certain storage conditions. Surprisingly, tablets made with Type II aripiprazole do not exhibit such a pronounced change in release profile after storage in a variety of conditions. Thus, tablets of the invention can have improved stability in comparison to the commercially available tablets.

The reasons for the instability in commercial aripiprazole tablets against, presumably aerial moisture and why the instability is expressed in acetate buffer and not in SGF are not clear at the present time. One hypothesis is that Type II aripiprazole can be relatively non-hygroscopic, a recently discovered property, in comparison to Type I, the presumed form of the commercial tablets. Regardless of the mechanism, it is clear that exposure of commercial aripiprazole tablets to open dish storage conditions adversely affects the dissolution. The commercial product apparently seeks to avoid this reduction in potential release of the drug in vivo by protecting the tablets from water via large amounts of desiccant and/or blister packaging. In contrast the present invention avoids or minimizes this problem by using a different crystalline form, namely the Type II form of aripiprazole.

Figure 1:
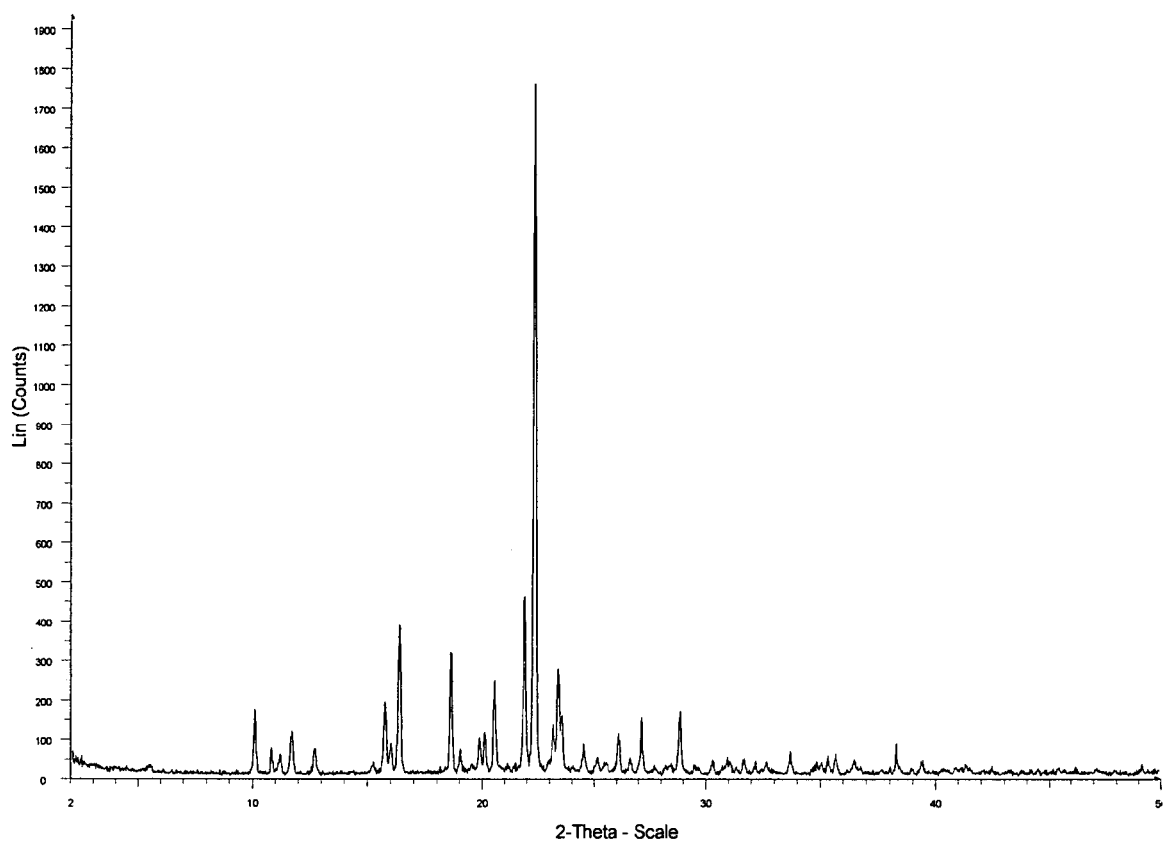
FIG. 1 represents an example of the XRPD pattern of aripiprazole Type II.

As used herein "Type II" of aripiprazole means a crystalline aripiprazole substance having an x-ray powder diffraction (XRPD) pattern that substantially corresponds to that of the Type II product as defined in the above cited article of Aoki. "Substantially corresponds" is meant to cover variations/differences in the pattern that would not be understood by a worker skilled in the art to represent a difference in crystal structure, but rather differences in technique, sample preparation, impurities, etc. An example of an XRPD of the Type II aripiprazole, and which thus substantially corresponds to the XRPD in Aoki, is shown on FIG. 1.

The Type II aripiprazole used in the present invention is of pharmaceutical grade, meaning that it is sufficiently pure and uniform so as to meet conventional pharmaceutical criteria for an active agent. In general the aripiprazole is at least 95% pure, and typically at least 99% pure of other, non-aripiprazole substances. The morphological purity is generally at least 70%, more typically at least 80%, and usually at least 90% of the Type II form.

The aripiprazole Type II generally is incorporated into the tablet composition in the form of particles having a particle size of 200 microns or less. For increasing the rate of dissolution, it is normally desired that the aripiprazole Type II have an average particle size of 50 microns or less, more typically 40 microns or less, and frequently 20 microns or less. Similarly, the population of particles typically has a $d_{90}$ of not greater than 70 microns, more typically not greater than 50 microns, and frequently less than 20 microns. For clarity, "$d_{90}$" refers to the particle size at which 90% of the particles have the same or a smaller particle size. A common particle size distribution of aripiprazole Type II for use in the present invention falls within the following ranges: $d_{10}$=0.1-5 microns; $d_{50}$=4-15 microns; and $d_{90}$=8-50 microns. Even though small particles of aripiprazole Type II are included in the above ranges, it has been discovered that the aripiprazole Type II population is not significantly hygroscopic and/or is non-hygroscopic. It is preferred that the aripiprazole Type II particles are formed in the desired size/population whereas milling larger aripiprazole Type II particles to obtain a desired smaller size is not preferred because it tends to cause and/or increase the hygroscopicity of the aripiprazole. It is believed that the increase in hygroscopicity caused by milling is due to changes in the crystalline structure to other crystalline forms and/or amorphous forms that are hygroscopic. Since hygroscopicity may be a part of the reason for the moisture sensitivity of the commercial tablets, it can be appreciated that any unnecessary or excessive increase in hygroscopicity should be avoided. Sieving is a preferred way to reduce the particle size, if necessary, as such activity generally has less effect on crystalline form. Thus, unmilled aripiprazole Type II, whether sieved or not, is generally preferred in order to maintain morphological purity and avoid hygroscopicity.

The aripiprazole Type II can be formulated into a pharmaceutical composition, especially a tablet, by combining the same with one or more pharmaceutically acceptable excipients. Generally the amount of aripiprazole is within the range of 1 to 50 mg per unit dose, and especially 2, 5, 10, 15, 20, 25, or 30 mg per tablet.

The tablet composition typically contains as pharmaceutically acceptable excipients: (a) one or more hydrophilic fillers especially polyol fillers, such as lactose, sorbitol, mannitol, etc.; (b) one or more binders, such as microcrystalline cellulose (MCC), hydroxylpropyl cellulose, hydroxylpropyl methylcellulose (HPMC), PVP, starch, etc.; (c) one or more disintegrants, such as sodium starch glycolate, crosspovidone, crosscarmelose sodium, etc.; and (d) a lubricant, such as magnesium stearate either alone or in combination with other lubricants. Typically the largest amount of the excipients is filler, accounting for at least 30% and generally at least 60% of all of the excipients by weight. The preferred filler is lactose monohydrate.

The tablet can be formed by any known or conventional process, including via wet granulation or direct compression. Typically, the tablets are formed via wet granulation wherein the aripiprazole Type II and at least one pharmaceutically acceptable excipient are granulated together with the aid of a granulation liquid, normally water or an aqueous solution, to form a granulate. A preferred wet granulation process is fluid bed granulation wherein a binder dissolved in a solvent, such as water, is combined with the aripiprazole Type II with rapid elimination of the solvent. However produced, the granulate is optionally mixed with additional excipient(s) and then compressed into tablets. Preferably, the extra-granular excipients also comprise a disintegrant to enhance the release rate after ingestion. A representative formulation for such tablets is shown below:

| Immediate Release Tablet | | |
|---|---|---|
| Ingredient | Wt % in Tablet | Function |
| Inter-granular | | |
| Aripiprazole Type II | 5-20% | Drug Substance |
| Sodium starch glycolate | 1-6% | Super disintegrant |
| MCC PH 101 | 0-25% | Binder/filler |
| Lactose monohydrate | 30-80% | Filler |
| Hydroxypropyl cellulose | 0-20% | Binder |
| Extra-granular | | |
| Sodium starch glycolate | 1-6% | Super disintegrant |
| Magnesium stearate | 0.5-3% | Lubricant |

Specific formulations for various dosage strengths are set forth below:

| | Percentage (%) | Strength (mg) | | | | |
|---|---|---|---|---|---|---|
| Strength (mg) | — | 5 | 10 | 15 | 20 | 30 |
| Inter-granular | | | | | | |
| Aripiprazole Type II | 10.53 | 5.0 | 10.0 | 15.0 | 20.0 | 30.0 |
| Sodium starch glycolate | 3 | 1.425 | 2.85 | 4.275 | 5.7 | 8.55 |
| MCC PH 101 | 10.53 | 5.0 | 10.0 | 15.0 | 20.0 | 30.0 |
| Lactose monhydrate | 70 | 33.25 | 66.5 | 99.75 | 133 | 199.5 |
| Hydroxyl propyl cellulose | 2.1 | 1.0 | 2.0 | 3.0 | 4.0 | 6.0 |
| Extra-granular | | | | | | |
| Sodium starch glycolate | 3 | 1.425 | 2.85 | 4.275 | 5.7 | 8.55 |
| Magnesium stearate | 0.84 | 0.4 | 0.8 | 1.2 | 1.6 | 2.4 |
| Target Tablet weight | — | 47.5 | 95 | 142.5 | 190 | 285 |
| Diameter (mm) | — | 5 | 6 | 7 | 8 | 9 |

The aripiprazole Type II used in the present invention can be made by any of the techniques disclosed in the above-recited patent applications and publications. In general it is preferred to use the methods of Provisional Application 60/692,557 and in particular the use of isopropanol or an approximately 1:1 by volume mixture of isopropanol and ethyl acetate as the solvent system from which aripiprazole Type II is precipitated. The solvent(s) is/are normally anhydrous, i.e. traces of water ordinarily present in a conventional batch should be controlled and, if necessary, removed. Typically the water content within the solvent system is less than 1%. The crystallization of aripiprazole as Type II from the solution can be carried out by techniques generally known in the art. Usually the crystallization involves cooling the solution. The nucleation may be improved by adding a seeding crystal(s) of Type II or scratching the surface of the vessel. The conditions of crystallization (concentration, cooling rate, etc.) may be controlled for the given solvent to result in the crystallization of aripiprazole Type II. The rate of cooling is not particularly limited but in general can be used to affect the particle size of the formed crystals. A quicker rate of cooling generally leads to smaller crystals. A spontaneous cooling rate; i.e., allowing the solution to cool without special cooling or heating measures, as well as a linear cooling rate are generally preferred, although other cooling regimes are also contemplated for use in the present invention. The final temperature after cooling may also affect the particle size, the yield and/or the purity of the product.

The present invention is more particularly described and explained by the following examples. It is to be understood, however, that the present invention is not limited to these examples and various changes and modifications may be made without departing from the scope of the present invention.

EXAMPLES

Reference Example 1

Formation of Aripiprazole Type II 140 g of aripiprazole was suspended in a mixture of 1 liter 2-propanol and 1 liter ethyl acetate. The stirred suspension was heated to reflux. A clear solution was obtained. Reflux was maintained for about 15 minutes. The stirred solution was allowed to cool to 55° C. At 55° C. the solution was seeded with 1 g of aripiprazole Type II crystals and precipitation commenced. The seeded solution was cooled to 4° C. in about 1 hour and 20 minutes. The resulting suspension was stirred at 0°-4° C. for 30 minutes. The solid was isolated by filtration and dried in a vacuum oven at 40° C., <10 mbar for 16 hours. The yield was 125 g (89%) of Type II aripiprazole.

Reference Example 2

Formation of Aripiprazole Type II 100 g Aripiprazole was suspended in 1.3 l of 2-propanol. The mixture was refluxed. After 1 hour a clear solution was obtained. The suspension was allowed to cool to room temperature, wherein at ±73° C. the solution was seeded with ±50 mg of Aripiprazol Type II crystals. Crystallization started at that temperature. Stirring was continued for 16 hours. The solid was isolated by filtration over a P3 glass filter. The solid was dried in a vacuum oven at 40° C. for 24 hours. Yield: 94 g Reference Example 3

Dissolution of Commercial Tablets

Samples of commercially available aripiprazole, sold under the brand name ALBILIFY® (Otsuka) (lot No. 4F4208A), were obtained and subjected to dissolution testing in both SGF and acetate buffer. These results are represented as "t=0". Additionally, some of the tablets were stored and later tested using the same dissolution tests. Specifically, some of the tablets were stored for one month at 40° C. in an open dish and some were stored for six months at 40° C. in a closed dish, namely in the original package. The results for these tests are referred to at "t=1" and t=6", respectively. The results are shown in below in FIGS. 2A and 2B.

Figure 2A:
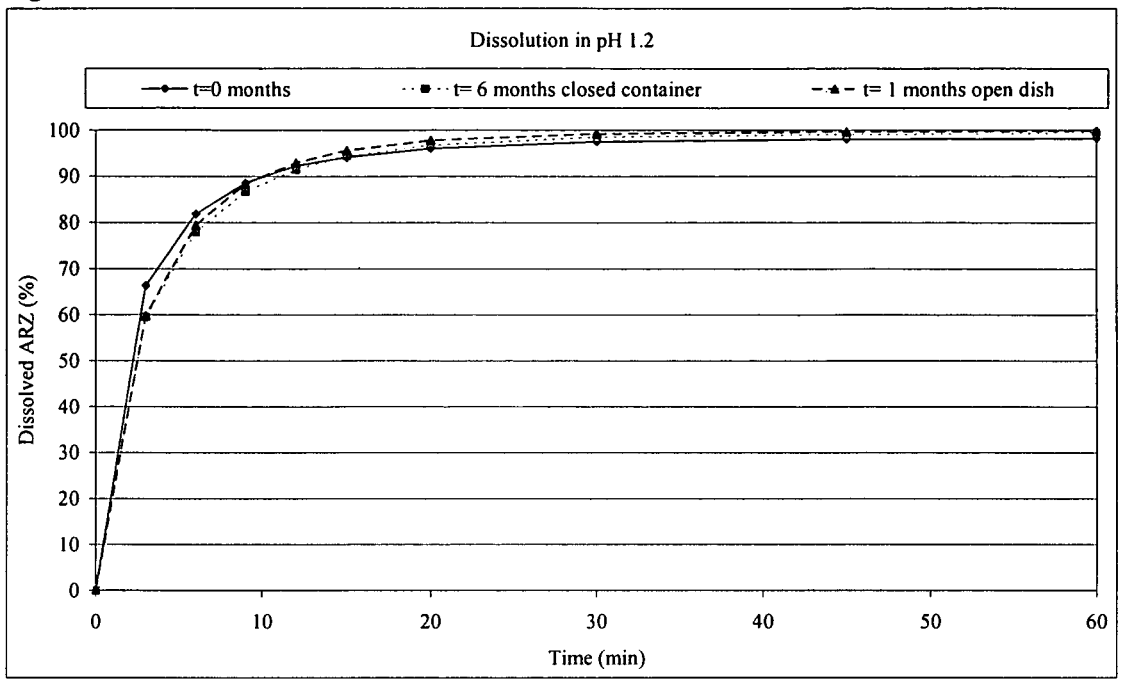
FIG. 2A shows the dissolution of commercial tablets from various storage conditions in pH 1.2 media. Dissolution profile (USP apparatus II) was measured in 900 ml SGF at a rotation speed of 60 rpm and a temperature of 37.5° C.
Figure 2B:
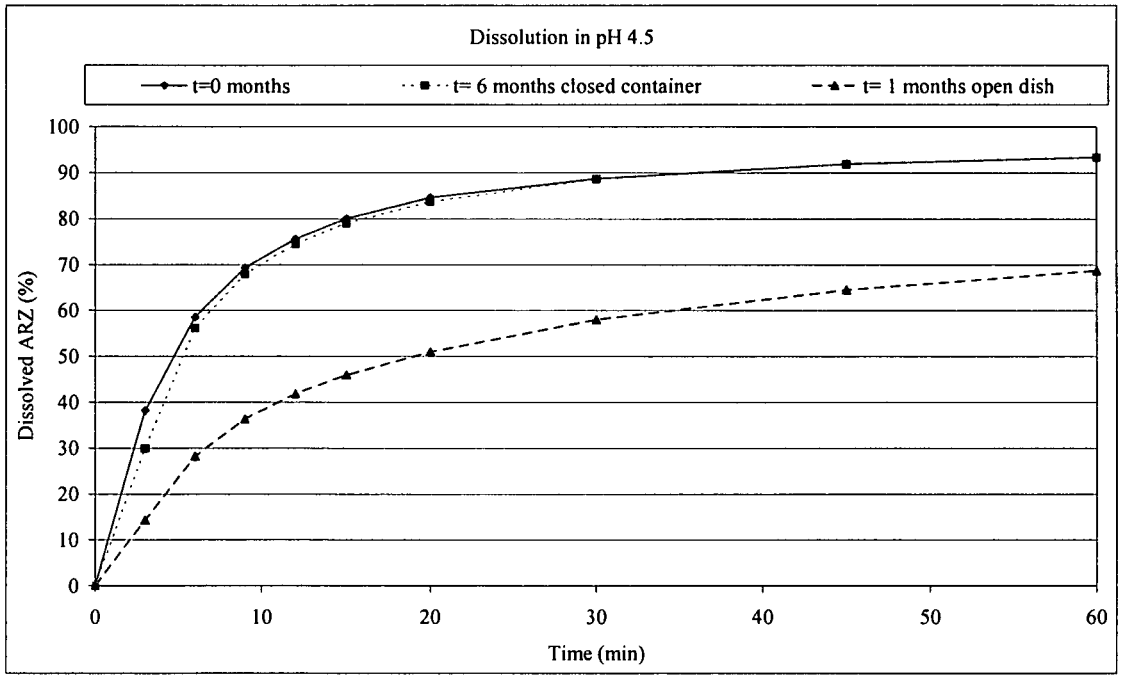
FIG. 2B shows the dissolution of commercial tablets from various storage conditions in pH 4.5 media. Dissolution profile (USP apparatus II) was measured in 900 ml acetate buffer pH 4.5 at a rotation speed of 60 rpm and a temperature of 37.5° C.

In comparing FIGS. 2A and 2B it is seen that storing the commercial tablets in open dish for only one (1) month significantly changed the release profile in acetate buffer, but not in SGF. In contrast, storing for six (6) months but in a closed container did not produce any significant change in dissolution profile for either acetate buffer or SGF.

Aripiprazole Type II Tablets
Tablets having the following composition were made having a hardness of 50 N and a diameter of 9 mm.

| Excipient | Unit weight (mg) | Percentage (%) |
|---|---|---|
| Inter-granular | | |
| Aripiprazole Type II | 30 | 10.53 |
| Sodium starch glycolate | 8.2 | 2.88 |
| MCC PH 101 | 30.0 | 10.53 |
| Lactose monohydrate | 199.8 | 70.11 |
| Hydroxyl propyl cellulose | 6.0 | 2.1 |
| (water)* | (114) | — |
| Extra-granular | | |
| Sodium starch glycolate | 8.6 | 3.02 |
| Magnesium stearate | 2.4 | 0.84 |
| Total | 285 | 100.02 |

*the water is removed during the granulation and drying steps

The tablets were made according to the following process on a 650 g scale using a Glatt GPCG 1.1:

Aripiprazole Type II (reference example 1), sodium starch glycolate (SSG), microcrystalline cellulose (MCC PH 101), and lactose monohydrate are put in the Glatt and fluidized (40-55 bar) for 5 minutes with an inlet temperature of 70° C. Hydroxylpropyl cellulose is dissolved in water to obtain a 5% solution. This solution is slowly sprayed (16 g/min) on the blend with an atomization air of 4 bar. Afterwards the granulate is dried for 30 min with an inlet temperature of 70° C.

The dried granulate is sieved through a 0.6 mm sieve and mixed with SSG for 15 minutes in a Turbula at 46 rpm. Magnesium stearate is added, sieved through a 0.8 mm sieve. Tablets are compressed on an EK-0 with a tablet weight of 285 mg, hardness of 50 N and a diameter of 9 mm.

The tablets were subjected to dissolution testing in SGF and acetate buffer as in Reference example 3 both immediately (t=0) and after the following storage conditions:

in container (HDPE bottles) at 40° C. with standard desiccant (2 g of desiccant)

in container at 40° C. without standard desiccant in open dish at 40° C.

in container with "2 sorb-it cans" at 40° C. (3 g of desiccant—same as in commercially available tablets)

Figure 3A:
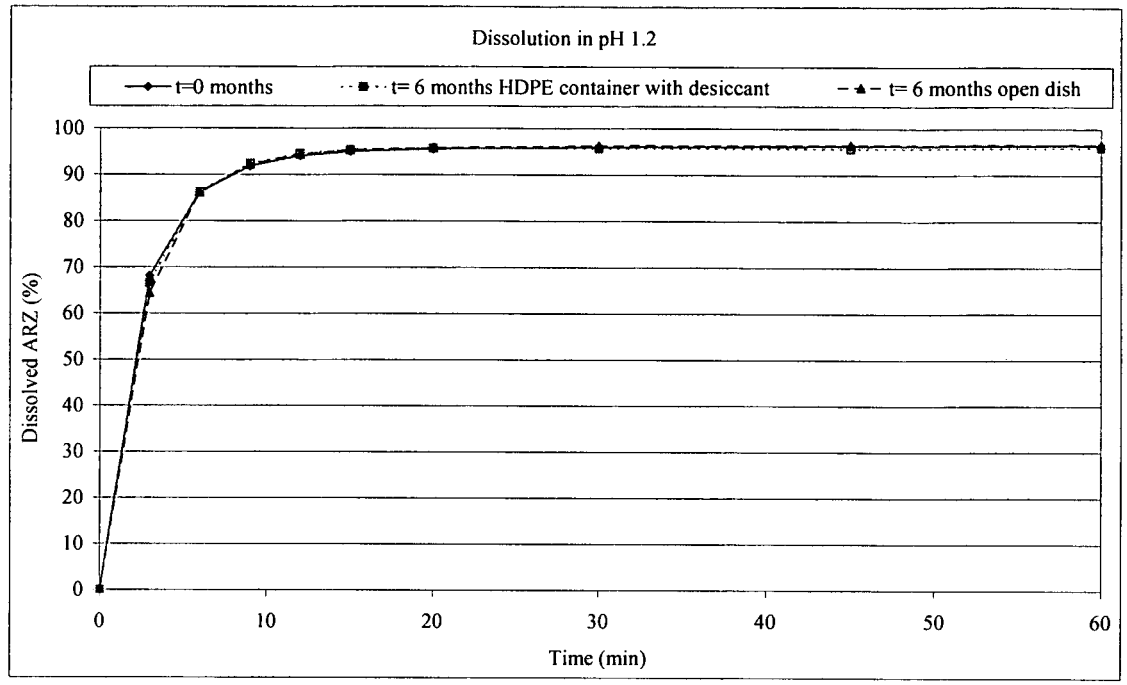
FIG. 3A shows the dissolution of inventive tablets from various storage conditions in pH 1.2 media. (The same conditions as in FIG. 2A)
Figure 3B:
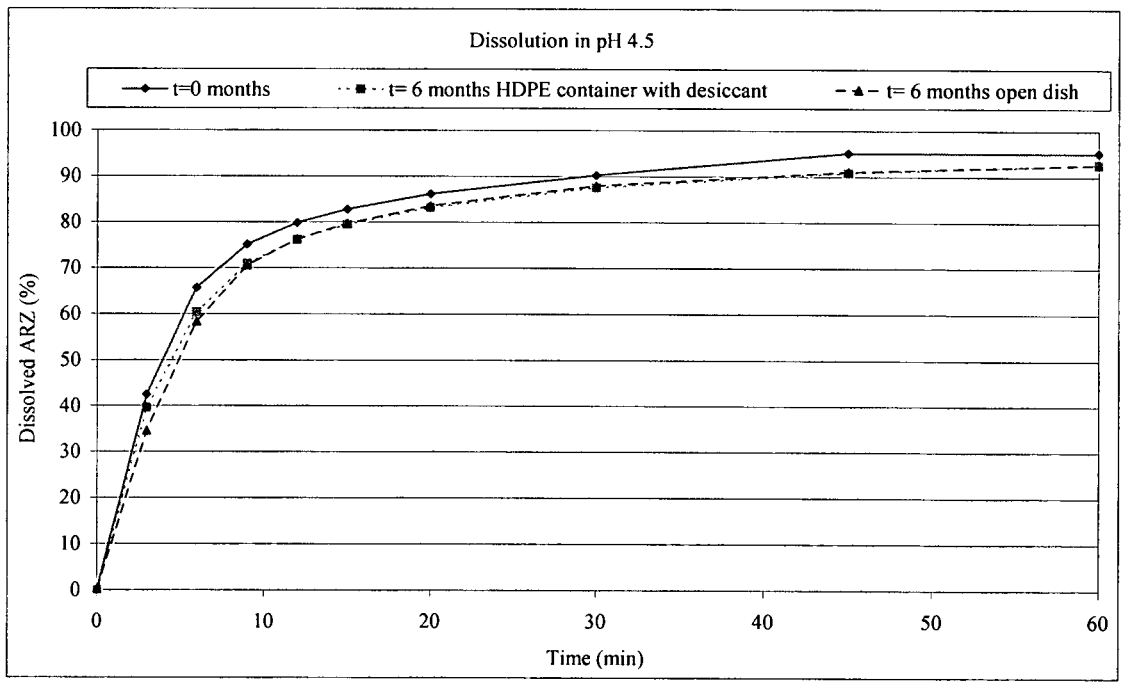
FIG. 3B shows the dissolution of inventive tablets from various storage conditions in pH 4.5 media. (The same conditions as in FIG. 2B)

The results in SGF pH 1.2 are shown in FIG. 3A and in acetate buffer pH 4.5 are shown in FIG. 3B.

The dissolution curves show that the tablets of the present invention, using aripiprazole Type II, do not show dissolution changes in response to various storage conditions. Instead the release remains relatively constant after a variety of storage conditions and even in acetate buffer. This means that the tablets of the invention may be more safe and/or can be more easily packaged; e.g., without the necessity of large amounts of desiccant, than the commercial tablets.

Example 2

Formulation for the 30 mg tablet

| Excipient | Unit weight (mg) | Percentage (%) |
|---|---|---|
| Inter-granular | | |
| ARZ Type II | 30 | 10.53 |
| Sodium starch glycolate | 8.55 | 3.0 |
| MCC PH 101 | 30.0 | 10.53 |
| Lactose monohydrate | 199.5 | 70 |
| Hydroxyl propyl cellulose (Klucel EF) | 6.0 | 2.1 |
| water* | 114 | — |
| Extra-granular | | |
| Sodium starch glycolate | 8.49 | 2.98 |
| Iron oxide red | 0.06 | 0.02 |
| Magnesium stearate | 2.4 | 0.84 |
| Total | 285 | 100.02 |

*is removed during the drying step

The tablets were made according to the following process on a 650 g scale using a Glatt GPCG 1.1

The Glatt was pre-heated for 5 minutes with an inlet temperature of 40° C. and a fluidization airflow of 100 m³/h. Aripiprazole Type II (reference Example 2, particle size $d_{50}$=5.0 microns, $d_{90}$=8.2 microns), sodium starch glycolate (SSG), microcrystalline cellulose (MCC) and lactose monohydrate were manually mixed and sieved through a 0.85 mm sieve. The mixture was put in the Glatt and fluidized (45 bar) for 3 minutes with an inlet temperature of 40° C. The inlet temperature was increased to 70° C. Hydroxy propyl cellulose was dissolved in water to obtain a 5% solution. This solution was slowly sprayed (16 g/min) on the blend with an atomization air of 4 bar when the inlet temperature reached the 70° C. Afterwards the granulate was dried for 30 minutes with an inlet temperature of 70° C.

All granulates were mixed with SSG and iron oxide for 7 minutes in the Turbula at 46 rpm. The mixture was sieved over a 0.6 mm sieve and mixed again for 7 minutes. Magnesium stearate was added sieved through a 0.8 mm sieve and the blend was mixed again for another 5 minutes at 22 rpm. Tablets were compressed on the EK-0 tablet press with a tablet weight of 285 mg, hardness of 40-45 N and a diameter of 9 mm.

Each of the patents, patent applications, and journal articles mentioned above are incorporated herein by reference. The invention having been described it will be obvious that the same may be varied in many ways and all such modifications are contemplated as being within the scope of the invention as defined by the following claims.

We claim:

1. A pharmaceutical composition in the form of a tablet, comprising 1 to 50 mg of aripiprazole Type II and pharmaceutically acceptable excipients, said excipients including (a) one or more polyol fillers, (b) one or more binders, (c) one or more disintegrants, and (d) a lubricant.

2. The composition according to claim 1, wherein said aripiprazole has a particle size distribution such that the $d_{90}$ is not greater than 50 microns.

3. The composition according to claim 2, wherein said aripiprazole is unmilled.

4. The composition according to claim 1, wherein said tablet is made by wet granulation.

5. The composition according to claim 1, wherein said polyol filler (a) is selected from lactose, sorbitol, mannitol, and combinations thereof.

6. The composition according to claim 5, wherein said polyol filler (a) is lactose monohydrate.

7. The composition according to claim 5, wherein said polyol filler (a) is contained in the greatest amount of said pharmaceutically acceptable excipients.

8. The composition according to claim 1, wherein said binder (b) comprises microcrystalline cellulose, hydroxypropyl cellulose or combinations thereof.

9. The composition according to claim 8 wherein said disintegrant (c) is sodium starch glycolate and said lubricant (d) is magnesium stearate.

10. The composition according to claim 9, wherein said polyol filler (a) is lactose monohydrate.

11. An aripiprazole pharmaceutical tablet made by a process, which comprises:
 wet granulating aripiprazole Type II with pharmaceutically acceptable excipients including (a) one or more polyol fillers, (b) one or more binders, and (c) one or more disintegrants to form a granulate;
 mixing said granulate with one or more additional pharmaceutically acceptable excipient(s) including at least (d) a lubricant to form a tablet blend; and
 compressing said tablet blend to form an aripiprazole pharmaceutical tablet.

12. The aripiprazole tablet according to claim 11, wherein said one or more additional pharmaceutically acceptable excipients in said mixing step further includes one or more disintegrants.

13. The aripiprazole tablet according to claim 12, wherein said granulate comprises:

| | |
|---|---|
| Aripiprazole Type II | 5-20% |
| Sodium starch glycolate | 1-6% |
| Microcrystalline cellulose | 0-25% |
| Lactose monohydrate | 30-80% |
| Hydroxylpropyl cellulose | 0-20% | and wherein said additional pharmaceutically acceptable excipients comprise:

| | |
|---|---|
| Sodium starch glycolate | 1-6% |
| Magnesium stearate | 0.5-3% | and wherein said percentages are based on the total weight of the aripiprazole tablet.

14. The aripiprazole tablet according to claim 11, wherein said aripiprazole Type II used in said wet granulating step was not milled and has a $d_{90}$ of 50 microns or less.

15. The aripiprazole tablet according to claim 13, wherein said aripiprazole Type II used in said wet granulating step was not milled and has a $d_{90}$ of 50 microns or less.

16. The composition according to claim 1, wherein said disintegrant (c) is selected from sodium starch glycolate, crosspovidone, crosscarmelose sodium, and combinations thereof.

17. The composition according to claim 1, wherein said pharmaceutically acceptable excipients consist essentially of (a) a filler selected from lactose, sorbitol, mannitol, and combinations thereof; (b) a binder selected from microcrystalline cellulose, hydroxypropyl cellulose, and combinations thereof; (c) a disintegrant selected from sodium starch glycolate, crosspovidone, crosscarmelose sodium and combinations thereof; and (d) a lubricant.

\* \* \* \* \*